US00PP33783P2

(12) United States Plant Patent
Cain

(10) Patent No.: US PP33,783 P2
(45) Date of Patent: Dec. 28, 2021

(54) SWEET CHERRY TREE NAMED 'IFG CHER-EIGHT'

(50) Latin Name: *Prunus avium*
Varietal Denomination: IFG Cher-eight

(71) Applicant: International Fruit Genetics LLC, Bakersfield, CA (US)

(72) Inventor: David Cain, Bakersfield, CA (US)

(73) Assignee: International Fruit Genetics, LLC., Bakersfield, CA (US)

( * ) Notice: Subject to any disclaimer, the term of this patent is extended or adjusted under 35 U.S.C. 154(b) by 0 days.

(21) Appl. No.: 17/102,658

(22) Filed: Nov. 24, 2020

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
See application file for complete search history.

*Primary Examiner* — Susan McCormick Ewoldt

(57) ABSTRACT

This invention is a new and distinct sweet cherry plant denominated 'IFG Cher-eight'. The new sweet cherry plant 'IFG Cher-eight' is characterized by producing large size medium dark red fruits having reniform shape. Fruits ripen early, have medium firm, medium acid fruit with a good cherry flavor and strong stem attachment. 'IFG Cher-eight' has a low chilling requirement and produces a high percentage of marketable fruit in warm climates.

1 Drawing Sheet

Latin name of the genus and species claimed: *Prunus avium.*

Variety denomination: 'IFG Cher-eight'.

CROSS REFERENCE TO RELATED APPLICATIONS

This application claims the benefit of Australian Plant Breeders Rights Appl. No. 2020/126, filed Jun. 30, 2020, herein incorporated by reference in its entirety.

BACKGROUND OF THE INVENTION

The new and distinct cherry described and claimed herein originated from open pollinated seeds of fruits of the unnamed female parent; IFG selection 01C059-023-378 (non-patented) growing near Delano, in Kern County, Calif. collected in May 2007. The male parent is unknown. The seeds were stratified, germinated and the resulting 17 seedlings were planted in the field near Delano, Kern County, Calif. in April 2008. The present variety of sweet cherry plant was selected as a single plant in May 2012 and was first asexually propagated in February 2013 by grafting onto *Prunus mahalab* rootstock. This propagule was found to reproduce true-to-type by asexual propagation. All propagation was done near Delano, Kern County Calif.

BRIEF SUMMARY OF THE INVENTION

Sweet cherries have traditionally been grown in climates with long cold winters and cool to moderately warm summers. Such climates provide enough cold winter temperatures to allow normal growth to resume in the spring and summer temperatures that are low enough not to induce production of unmarketable double or spurred fruit, but it limits the seasonality that sweet cherries are available. The IFG sweet cherry breeding program focuses on developing types of cherries that will grow in regions with low winter chilling and high summer temperatures so that the fruit will ripen before fruit in traditional growing regions.

The new sweet cherry plant 'IFG Cher-eight' is characterized by producing large size medium dark red fruits having reniform shape. Fruits ripen early, have medium firm, medium acid fruit with a good cherry flavor. 'IFG Cher-eight' has a high percentage of marketable fruit. Fruit stems are long, medium thick and have strong attachment and stay green during storage and shipping.

'IFG Cher-eight' is self-incompatible having S1S6 pollen alleles. The plant has a low chilling requirement of about 300 to 400 hours. It produces very few doubled and spurred fruits in high summer temperature regions such as the Southern San Joaquin Valley of California.

The cherry varieties believed to be most similar to 'IFG Cher-eight' are 'Brooks' (U.S. Plant Pat. No. 6,676) and 'IFG Cher-three' (U.S. Plant Pat. No. 30,011). 'Brooks' (U.S. Plant Pat. No. 6,676) is a major cherry variety grown in warm regions. 'IFG Cher-eight' ripens with or slightly earlier than 'Brooks'. Nonetheless, 'Brooks' and 'IFG Cher-eight' are distinguishable at least in their fruit production and chilling requirement. Specifically, 'IFG Cher-eight' has fewer undesirable doubled and spurred fruits and has superior stem attachment and storage characteristics. Additionally, 'IFG Cher-eight' has a lower chilling requirement than 'Brooks' and can be successfully grown in lower chill regions where 'Brooks' cannot be grown.

In comparison to 'IFG Cher-three,' 'IFG Cher-eight' has a similar chilling requirement. Nonetheless, 'IFG Cher-three' and 'IFG Cher-eight' are distinguishable at least in their ripening time and fruit characteristics. Specifically, 'IFG Cher-eight' ripens five to seven days later, has larger fruit size, lighter flesh and skin color, and is softer. Additionally, 'IFG Cher-eight' exhibits less pebbling of the skin surface and better stem quality during long term storage as compared to 'IFG Cher-three'.

In comparison to its female parent, IFG selection 01C059-023-378, 'IFG Cher-eight' has larger, firmer fruits, darker flesh and skin color, and a shorter thicker stem.

BRIEF DESCRIPTION OF THE DRAWING

The accompanying photographic drawing illustrates in full color 'IFG Cher-eight', taken from a 6-year old tree. The photograph was taken outdoors with indirect lighting The colors are as nearly true as is reasonably possible in a color representation of this type.

FIG. 1—Shows an actively growing shoot tip in the upper portion of the drawing Typical mature fruit, fruit in cross section and cleaned and dried fruit pits are displayed in the lower half of the drawing.

DETAILED BOTANICAL DESCRIPTION OF THE INVENTION

Throughout this specification, color names beginning with a small letter signify that the name of that color, as used in common speech, is aptly descriptive Color names beginning with a capital letter designate values based upon R.H.S. Colour Chart, published in 2001 by The Royal Horticultural Society, London, England Throughout this specification, subjective description values conform to those set forth by the International Board for Plant Genetic Resources (IBPGR) 'Cherry Descriptor List' (*Prunus* spp) (1985) which was developed with full support from the Commission of the European Communities (CEC) Programme Committee for Plant Disease Resistance Breeding and the Use of Genebanks The descriptive matter which follows pertains to 'IFG Cher-eight' plants grown in the vicinity of Delano, Kern County, Calif. during 2018 and 2019, and is believed to apply to plants of the variety grown under similar conditions of soil and climate elsewhere:

Tree:

*General*.—Age of plant when data collected — 6-yrs-old. Height — Approximately 2.8 M when pruned. Width — Approximately 1.8 M when pruned. Size — Medium. Vigor — Moderately strong. Density of foliage — Medium. Form — Spreading. Branching — Medium. Root stock — Own root. Resistance to — Insects: Average typical of *Prunus avium* species. Diseases: Average typical of *Prunus avium* species. Chilling Requirements — Very low to Low. Graft Compatibility — Good: produces compatible graft unions with *Prunus avium*, 'Mazzard' seedling (non-patented) and *Prunus Mahaleb* seedlings (non-patented).

*Trunk*.—Trunk diameter of 6-year-old tree, 30 cm above the soil line — Approximately 12.8 cm. Lenticel Size — Medium. Lenticel dimensions — Length: About 1.1 cm. Width: About 0.3 cm. Lenticel Shape — Elliptical shape, oriented horizontally. Lenticel Color — Greyed-green: 197B. Trunk Surface texture — Slight to moderate roughness. Outer bark color — Greyed-purple: 187A.

Branches:

*Young shoots*.—Anthocyanin coloration of apex (during rapid growth) — Absent or very weak. Pubescence of apex (during rapid growth) — Weak.

1-*year-old wood*.—Vertical top growth length — Medium: About 54 cm. Horizontal growth length — Medium: About 24 cm. Diameter — Vertical growth: About 0.8 cm. Horizontal growth: About 0.5 cm. Internode length — Medium: About 3.0 cm. Number of lenticels — Few to medium: About 9 lenticels per linear cm. Lenticel Size — Small. Lenticel dimensions — Length: About 0.5 mm. Width: About 0.5 mm. Lenticel shape — Round. Bark color — Greyed-orange: 175A.

2-*year-old wood*.—Length — Medium: About 23.7 cm. Diameter — About 0.7 cm. Internode length — Medium: About 4.0 cm. Number of Lenticels — Few to medium: About 7 lenticels per linear cm. Lenticel dimensions — Length: About 0.5 mm. Width: About 0.5 mm. Lenticel shape — Round. Number of fruiting spurs — Approximately 11. Bark Color — Greyed-orange: 175A.

Buds:

*Vegetative buds*.—Shape — Elongated. Vegetative bud dimensions — Length: About 7.1 mm. Width: About 3.3 mm. Color — The following colors were observed: Greyed-orange: 166A and 166B and 166C.

*Flower buds*.—Flower bud dimensions — Length: About 9.0 mm. Width: About 4.2 mm. Shape — Rounded oval. Placement — At bud positions mostly 1 to 10 on 1-year wood. Average number of flower buds on first year wood: About 8. Number of Flower buds per spur on second year wood — 6 to 9. Average about 7. Color — The following colors were observed: Greyed-orange: 166A and 166B and 166C. Flower bud burst — About Feb. 19, 2019.

Leaves:

*Mature leaves*.—Leaf dimensions — Length: Long: About 18.6 cm. Width: Broad: About 7.9 cm. Leaf shape — Lanceolate: Symmetric on both sides of central axis. Shape of tip — Acuminate: broadly. Shape of base — Rounded. Margin — Serrated: Regular: Pointed. Leaf profile — V-shaped. Venation — Arcuate. Vein Color — Yellow-green: 145B.

*Upper surface*.—Upper surface pubescence — None. Upper leaf surface color — Green: 137A. Surface texture — Medium.

*Lower surface*.—Lower surface Pubescence — Moderately dense: All over. Lower leaf surface color — Yellow green: 147B.

*Petiole*.—Petiole dimensions — Length: About 3.2 cm. Width: About 2.6 mm. Upper surface of petiole color — The following colors were observed: Yellow-green: 146C and Greyed-purple: 184A. Lower surface of petiole color — Yellow-green: 145B. Petiole groove — Narrow: Approximately 0.6 mm. Petiole Pubescence — Very sparse to sparse on both upper and lower surfaces.

*Glands*.—Number of glands — About 2. Gland dimensions — Length: About 2.4 mm. Width: About 1.1 mm. Gland shape — Mixture of globose and reniform. Gland location — On petiole. Gland Color — The following colors were observed: Yellow-green: 145C and Greyed-purple: 184C. Leaf Stipule — Present.

Flowers:

*Blooming period*.—Early.

*Blooming dates*.—First Bloom: About Feb. 28, 2019. Full Bloom: About Mar. 13, 2019.

*Number of flowers per cluster*.—3 to 6. Average: About 4.2.

*Corolla*.—Composed of unfused petals, slightly overlapping.
*Corolla diameter*.—About 3.2 cm.
*Petal number*.—5.
*Petal shape*.—Broad obovate.
*Petal length*.—About 1.7 cm.
*Petal width*.—About 1.8 cm.
*Margin waviness*.—Medium.
*Division of upper margin*.—Notched.
*Color of petal upper surface*.—White: N155A.
*Color of petal lower surface*.—White: N155A.
*Peduncle*.—Length: About 1.8 cm. Width: About 1.2 mm.
*Peduncle color*.—Yellow-green: N144B.
*Number of sepals*.—5.
*Sepal length*.—About 0.9 cm.
*Sepal width*.—About 0.5 cm.
*Sepal shape*.—Ovate.
*Sepal color*.—Outer surface — The following colors were observed: Yellow-green: N144B and Greyed-purple: 187B.
*Sepal color*.—Inner surface — The following colors were observed: Yellow-green: N144C and N144D.
*Filament*.—Length: Approximately 0.7 to 1.4 cm. Width: Approximately 0.5 mm.
*Filament color*.—White: N155A.
*Anther color*.—Yellow: 10A.
*Pollen color*.—Yellow: 11A.
*Pollen production*.—High.
*Self-compatibility of flowers*.—Self-incompatible.
*Pollen compatibility group*.—S1S6.

Fruit:

*General*.—Ripening period — Early: Approximately: May 9, 2019. Use — Fresh market. Keeping quality — Good. Refractometer test — Soluble solids: Brix: About 14.8. Firmtech II (g/mm) — About 309. Flavor — Good. Eating quality — Good.
*Stem*.—Stem — Length: About 5.5 cm. Width: About 1.3 mm. Stem color — Yellow-green: 144A. Stem cavity — Narrow. Stem pull force — About 506 g. Stem retention during storage — Excellent. Stem storage quality — Good.
*Berry*.—Uniformity of size — Uniform. Shape — Reniform. Pistil end — Flat. Fruit Weight — About 10.1 gm. Apical Diameter — About 2.5 cm. Diameter transversely across suture — About 2.4 cm. Diameter at right angle to suture plane — About 2.7 cm. Suture — Absent. Percent of excessively deep or split sutures — About 0%. Doubles — About 0%.
*Skin*.—Texture — Smooth. Skin Color — Greyed-purple: 187A. Tendency to crack — Slight to moderate.
*Flesh*.—Texture — Firm. Color — Greyed-purple: 187C. Stone cavity color — Greyed-purple: 187A.
*Stone*.—Shape — Broadly elliptic. Length — About 10.7 mm. Width across suture — About 6.5 mm. Width at right angle to suture plane — About 9.3 mm. Dry stone weight — About 0.23 gm. Type — Clingstone. Surface texture — Slightly rough. Stone Color when dry — Orange-white: 159A. Tendency to split — None. Base — Rounded. Apex — Rounded. Ventral edge — Narrow suture subtended by two less prominent ridges converging at base and apex. Dorsal edge — Smooth, narrow ridge from base to apex.

What is claimed is:

1. A new and distinct variety of sweet cherry tree named 'IFG Cher-eight', as herein illustrated and described.

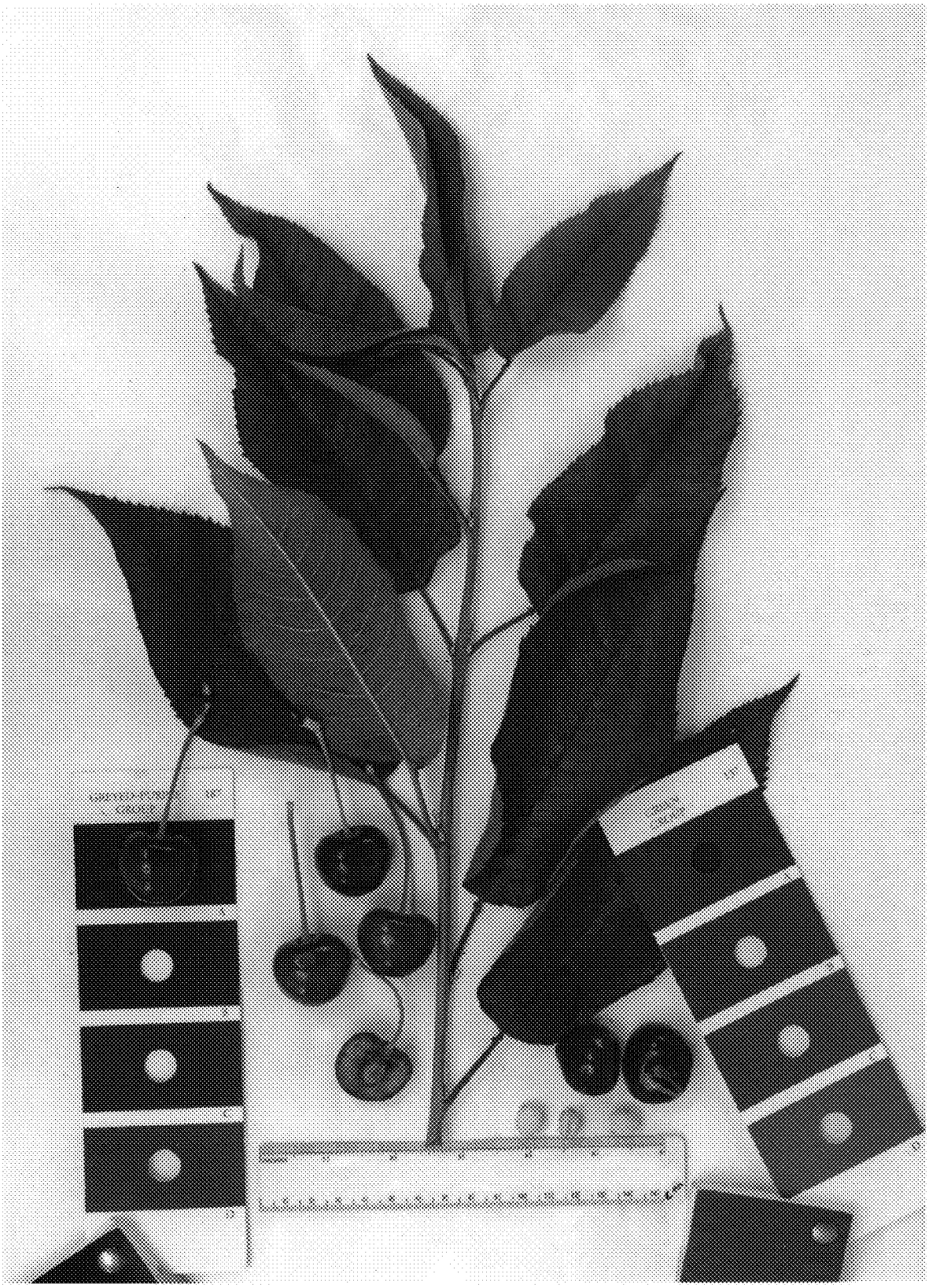

* * * * *